United States Patent [19]

Siadak et al.

[11] Patent Number: 4,834,975
[45] Date of Patent: May 30, 1989

[54] HUMAN MONOCLONAL ANTIBODIES TO SEROTYPIC LIPOPOLYSACCHARIDE DETERMINANTS ON GRAM-NEGATIVE BACTERIA AND THEIR PRODUCTION

[75] Inventors: Anthony W. Siadak, Seattle; Mark E. Lostrom, Redmond, both of Wash.

[73] Assignees: Genetics Corporation, Seattle, Wash.; Miles, Inc., Elkhart, Ind.

[21] Appl. No.: 734,624

[22] Filed: May 15, 1985

Related U.S. Application Data

[63] Continuation-in-part of Ser. No. 614,184, May 25, 1984, abandoned.

[51] Int. Cl.$^4$ .................. A61K 39/40; C07K 15/00; C12N 5/00
[52] U.S. Cl. .................. 424/87; 530/387; 530/388; 435/7; 435/68; 435/70; 435/172.2; 435/172.3; 435/240.2; 435/948; 935/100; 935/107; 935/52; 935/71; 436/548
[58] Field of Search .................. 530/387, 388; 424/87; 435/7, 68, 70, 172.2, 172.3, 240, 241, 172.1, 948, 240.2, 240.27; 935/99, 100, 107, 110, 52, 71; 436/548

[56] References Cited

U.S. PATENT DOCUMENTS 4,464,465  8/1984  Lostrom .................. 435/68

FOREIGN PATENT DOCUMENTS 0057107  8/1982  European Pat. Off. .
0101039  2/1984  European Pat. Off. .
0105804  4/1984  European Pat. Off. .
WO8404458  11/1984  PCT Int'l Appl. .
WO8501659  4/1985  PCT Int'l Appl. .

OTHER PUBLICATIONS

Koskimies, S., Scand. J. Immunology, 11: 73–77 (1980).
Steinitz, M. et al., J. Immunology, 132(2): 877–882 (2-1984).
Hancock, R. E. W. et al, Infect. Immun., 37(1):166-171 (7-1982).
Mackie, E. B. et al, J. Immunology, 129(2):829-32 (1982).
Darveau R. P. et al. J. Bacteriology, 155(2):831-8 (8-1983).
Lam, J. S. et al, Infect. Immun., 42(1):88-98 (10-1983).
Luderitz, O., et al., "Isolation and Chemical and Immunological Characterization of Bacterial Lipopolysaccharides," *Microbial Toxins,* 4:145-233.
Teng, N. N. H., et al., "Protection against Gram-negative Bacteria and Endotoximia with human monoclonal (List continued on next page.)

*Primary Examiner*—Margaret Moskowitz
*Attorney, Agent, or Firm*—Townsend and Townsend

[57] ABSTRACT

Transformed human lymphocyte cell lines have been produced which secrete human monoclonal antibodies to serotypic determinants on LPS molecules of gram-negative bacteria. These antibodies have been found to be protective against lethal challenges of the homologous bacteria. Pharmaceutical compositions containing these antibodies and their prophylactic and therapeutic use in the management of gram-negative disease in humans are also disclosed.

Human lymphocyte cell lines secreting human monoclonal antibodies specifically reacting with *Pseudomonas aeruginosa* Fisher immunotypes 1 (C5B7), 2 (6F11), 4 (C5D5), 5 (13C1), 6 (5G2) and 7 (8E7) were deposited at the American Type Culture Collection and given A.T.C.C. Accession Nos. CRL 8753, CRL 8562, CRL 8754, CRL 8796, CRL 8797 and CRL 8795, respectively.

15 Claims, 1 Drawing Sheet

OTHER PUBLICATIONS

IgM Antibodies," P.N.A.S. U.S.A. (1985) 82:1790–1794.

Hornberger, E., et al., Federation of American Societies for Experimental Biology, 69th Annual Meeting, (1985), Abstract of Papers, abstract No. 5366.

Westphal, O., et al., "Chemistry and Immunochemistry of Bacterial Lipopolysaccharides as Cell Wall Antigens and Endotoxins," *Prog. Allergy* (1983) 33:9–39.

Agarwal, M. K., "Bacterial Endotoxions and Host Responses," Proc. of the 4th Int'l Congress of Immunology, Satellite Workshop, Paris, France, Jul. 1980, pp. 79–93.

Hanessian, S., et al., "Isolation and Characterization of Antigenic Components of a New Heptavalent Pseudomonas Vaccine," Letters to Nature (Feb. 1971) *Nature New Biology*, 229:209–210.

Sadoff, J., et al., Abstract No. 253, Program and Abstracts of the Twenty-Second Interscience Conference on Antimicrobial Agents and Chemotherapy, Sponsored by American Society for Microbiology, Oct. 4–6, 1982, Miami Beach, Florida.

Zinner, S. H., and McCabe, W. R., "Effects of IgM and IgG Antibody in Patients with Bacteremia Due to Gram–Negative Bacilli," *J. Infect. Dis.* (1976) 133(a):37–45.

Pollack, M. and Young, L. S., "Protective Activity of Antibodies to Endotoxin A and Lipopolysaccharide at the Onset of Pseudomonas aeruginosa Septicemia in Man," *J. Clin. Invest.* (1979) 63:276–286.

Morrison, D. C. and Ryan, J. L., "Bacterial Endotoxins and Host Immune Responses," *Adv. in Immun.* (1979) 28:293–450.

Fisher, et al., "New Immunotype Schema for Pseudomonas aeruginosa Based on Protective Antigens," J. of Bacteriology (1969) 98:(2)835–836.

Pollack, M., "Antibody–Mediated Immunity in Pseudomas Disease and its Clinical Applications," Department of Medicine, Uniformed Services University, Bethesda, Maryland 20014, USA., pp. 73–79.

Sawada et al., J. Infect. Dis. (1984) 150:570–576.

●,○:Monosaccharide, •:Phosphate, ⌒ :Ethanolamine
——:Long Chain (Hydroxy) Fatty Acid

HUMAN MONOCLONAL ANTIBODIES TO SEROTYPIC LIPOPOLYSACCHARIDE DETERMINANTS ON GRAM-NEGATIVE BACTERIA AND THEIR PRODUCTION

CROSS-REFERENCE TO RELATED APPLICATIONS

This application is a continuation-in-part of application Ser. No. 614,184, filed May 25, 1984, now abandoned, which disclosure is incorporated herein by reference.

BACKGROUND OF THE INVENTION

1. Field of the Invention

Gram-negative bacterial disease and its most serious complications, e.g., bacteremia and endotoxemia, are the cause of significant morbidity and mortality in human patients.

An examination of many of the cases documented in the literature indicates that some of the manifestions of infection with gram-negative bacteria, especially lethal manifestations are associated with certain predisposing factors. There is an increased incidence of such infections in elderly patients and in patients who have serious underlying medical conditions such as burns, surgical trauma, slow-healing wounds, narcotic addiction, or malignancies. These infections may be of nosocomial (i.e., hospital-acquired) origin in patients who have sustained prolonged hospitalization, and particularly in patients who have been subjected to surgical intervention, intravascular instrumentation, or manipulative procedures such as urethral catheterizations, cystoscopies, tracheostomies, lumbar puncture, and intravenous infusion of medications and fluids or who have been placed on long-term therapy with immunosuppressive agents, corticosteroids, antimetabolites, and/or antibiotics. Radiation therapy also predisposes a mammalian host to infection by gram-negative bacteria.

Included amoung the most frequently encountered organisms in gram-negative disease are *Escherichia coli*, *Klebsiella pneumoniae*, *Enterobacter aerogenes*, *Pseudomonas aeruginosa*, *Serratia marcescens*, and various species of *Proteus*, *Bacteroides*, *Providencia*, and *Citrobacter* (Sonnenwirth, "The Enteric Bacilli and Similar Gram-Negative Bacteria," pp. 753–790, *Microbiology*, 2nd edition, Davis, B. D., Dulbecco, R., Eisen, H. N., Ginsberg, H. S., Wood, W. B., and McCarty, M., eds., Harper and Row (1973); McCabe, W. R., "Gram-Negative Bacteremia," *Adv. Intern. Med.* (1974) 19:135–158; and Kreger et al., "Gram-Negative Bacteremia III. Reassessment of Etiology, Epidemiology and Ecology in 612 Patients," *Am. J. Med.* (1980) 68:332–343). Also, other species of *Pseudomonas* and *Klebsiella* as well as members of the genera *Aeromonas*, *Salmonella*, *Flavobacterium*, *Erwinia*, *Edwardsiella*, *Pectobacterium*, *Acinetobacter*, *Alcaligenes*, and *Shigella* contribute to a significant proportion of gram-negative disease in humans (Sonnenwirth, supra; McCabe, supra; Kreger et al supra).

During the past few decades, antibiotics have been the therapy of choice in the control of gram-negative bacterial disease. The continued prevalence and high morbidity and mortality associated with gram-negative bacterial disease, however, suggest limitations of antibiotic therapy to prevent and treat disease by these organisms. See, for example, Andriole, V. T., "*Pseudomonas* Bacteremia: Can Antibiotic Therapy Improve Survival?", *J. Lab. Clin. Med.* (1978) 94:196–199. This has prompted the search for alternative prevention and treatment methods.

2. Description of the Prior Art

Active immunization of man or experimental animals with whole bacterial cell vaccines or purified bacterial endotoxins leads to the development of specific antibodies directed mainly against the chemically diverse repeating oligosaccharide determinants present on lipopolysaccharide (LPS) molecules (Luderitz et al., "Immunochemistry of O and R Antigens of *Salmonella* and Related *Enterobacteriaceae*," *Bacteriol. Rev.* (1966) 30:192–255; and Luderitz et al., "Isolation and Chemical and Immunological Characterization of Bacterial Lipopolysaccharides," *Microbial Toxins*, Vol. 4, pp. 145–233, Weinbaum, G., Kadis, S., and Ajl, S. J., eds., Academic Press (1977), see FIG. 1). In this regard, it is important to note that LPS molecules are one of the major constituents of the outer cell membrane of most, if not all, gram-negative bacteria (Nikaido, H., "Biosynthesis and Assembly of Lipopolysaccharide," *Bacterial Membranes and Walls*, Leive, L., ed., Marcel Decker, (1973); see FIG. 2). In FIG. 1 is illustrated a model of the gram-negative cell wall showing the position of lipopolysaccharide molecules with respect to the outer membrane of the bacterium. This model is devoid of structures such as capsules, envelopes and slime layers.

Lipopolysaccharides are also integral constituents of bacterial endotoxins, with the lipid A moiety of LPS molecules being responsible for the profound pathophysiologic effects (e.g., fever, hypotension, disseminated intravascular coagulation, shock, and potentially death) associated with endotoxin release during gram-negative bacterial septicemia or induced experimentally with injections of endotoxin (Westphal et al., "Chemistry and Immunochemistry of Bacterial Lipopolysaccharides as Cell Wall Antigens and Endotoxins," *Prog. Allergy* (1983) 33:9–39). FIG. 2 illustrates the three regions of gram-negative lipopolysaccharides. The O-specific chain region is a long-chain polysaccharide built up from repeating oligosaccharides units. In different bacterial species these oligosaccharide units may contain from 1 to as many as 6 or 7 monosaccharide units. Serotypic determinants of LPS (see text) are displayed on this region of the molecule. The core region contains several monosaccharides in arrangements that are relatively invariant from one strain of gram-negative bacteria to another. The lipid A region is virtually the same in all gram-negative bacteria, is generally attached to the core region through the keto-deoxyoctonic acid moiety, and serves as the attachment point of the lipopolysaccharide molecule to the outer membrane.

The induction and immunotherapeutic use of type-specific anti-LPS antibodies have been most extensively studied in the treatment of disease due to *Pseudomonas aeruginosa* (*P. aeruginosa*) because of its high degree of antibiotic resistance. Such antibodies, whether actively engendered or passively transferred, have been shown to be protective in a variety of animal infection models. For a review, see Pollack, M., "Antibody-Mediated Immunity in Pseudomonas Disease and Its Clinical Application," *Immunoglobulins: Characteristics and Uses of Intravenous Preparations*, Alving, B. M. and Finlayson, J. S., eds., pp. 73–79, U.S. Department of Health and Human Services, (1979).

Perhaps more importantly, high acute serum titers of antibodies to the type-specific portions of LPS molecules of infecting strains have been observed to be associated with survival in patients with *P. aeruginosa* bacteremia (Pollack, M. and Young, L. S., "Protective Activity of Antibodies to Exotoxin A and Lipopolysaccharide at the onset of *Pseudomonas aeruginosa* Septicemia in Man," *J. Clin. Invest.* (1979) 63:276-286). This observation has, in fact, been found to extend to the majority of bacteremias caused by various gram-negative organisms (Zinner, S. H. and McCabe, W. R., "Effects of IgM and IgG Antibody in Patients with Bacteremia Due to Gram-Negative Bacilli," *J. Infect. Dis.* (1976) 133:37-45; and Clumeck et al., "Humoral Immunity and Circulating Immune Complexes in Gram-Negative Bacteremia and Septic Shock," *Bacterial Endotoxins and Host Response*, pp. 79-94, Agarwal, M. K., ed., Elsevier, (1980)).

Although the precise means by which anti-LPS antibodies exert such protection have not been entirely delineated (particularly with respect to the various genera of gram-negative bacteria), it is generally thought that they do so by faciliating clearance of LPS molecules from the bloomstream by the reticuloendothelial system or by rendering LPS containing bacteria sensitive to complement-mediated lysis and/or phagocytosis (Morrison, D. C. and Ryan, J. L., "Bacterial Endotoxins and Host Immune Responses," *Adv. Immunol.* (1979) 28:293-450). Conceivably, any one or a combination of the above protection schemes may be at work in serious gram-negative bacterial disease.

In 1975 Kohler and Milstein reported their discovery that certain mouse cell lines could be fused with mouse spleen cells to create hybridomas which would secrete pure "monoclonal" antibodies (Kohler, G., and Milstein, C., "Continuous Cultures of Fused Cells Secreting Antibody of Predefined Specificity," *Nature* (1975) 256:495-497).

In a 1982 abstract (#253) published on p. 110 of the *Abstracts of the* 1982 *Interscience Conference on Antimicrobial Agents and Chemotherapy*, J. Sadoff et al., reported the production, via hybridoma techniques, of mouse (murine) monoclonal antibodies of the IgM class directed against the oligosaccharide determinants of the LPS molecules of a particular strain (serotype) of *P. aeruginosa* and that these murine monoclonal antibodies provided protection to mice against a lethal challenge of *P. aeruginosa* bacteria of the same strain (i.e., the homologous strain).

SUMMARY OF THE INVENTION

Novel human transformed lymphocyte cell lines and human monoclonal antibodies are provided, where the cell lines and antibodies specifically bind to certain serotypic determinants on the lipopolysaccharide (LPS) molecules of the outer cell membrane(s) of gram-negative bacteria. The monoclonal antibodies may be used for protection in mammals against a lethal challenge of homologous gram-negative bacteria and should permit the therapeutic and/or prophylactic treatment of the pathophysiologic effects of gram-negative bacterial disease in humans.

DETAILED DESCRIPTION OF THE INVENTION

Figure 1:
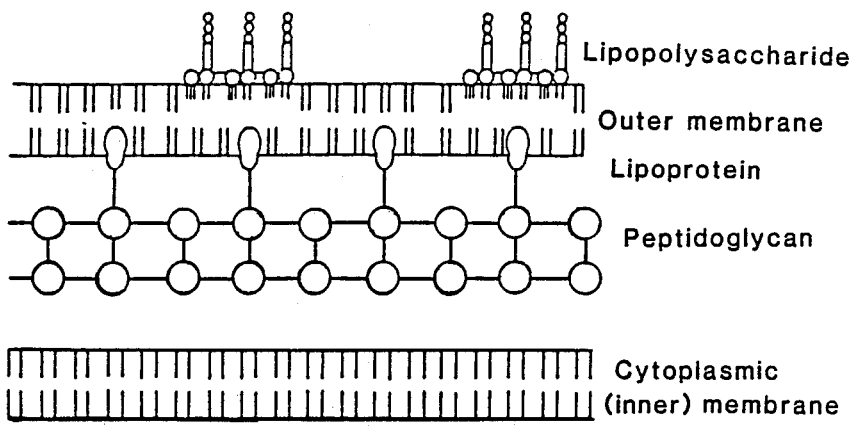
FIG. 1 is an illustrative diagram of the membranes and inner wall of gram-negative bacterium.
Figure 2:
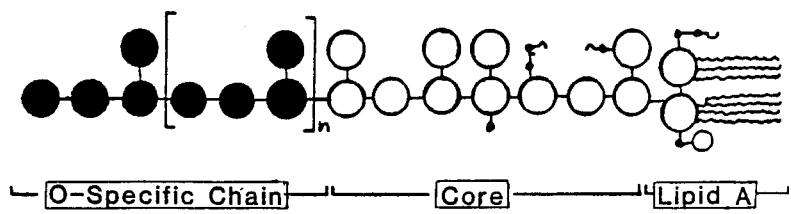
FIG. 2 is a schematic depiction of a lipopolysaccharide molecule.

Human transformed lymphocyte cells are provided which produce specific protective human monoclonal antibodies to accessible lipopolysaccharide molecules. By "accessible" is meant that the LPS molecules are physically available in the environment of use for direct interaction with the monoclonal antibodies. By this definition, LPS molecules that are shed from gram-negative bacteria into the surrounding environment would be free to interact directly with specific monoclonal antibody and be cleared via the reticuloendothelial system. In this context, monoclonal antibodies would be expected to be of benefit in the treatment of serious disease due to a wide variety of gram-negative bacteria. Additionally, LPS molecules residing on the outer surface of gram-negative bacteria would be available for direct contact with specific monoclonal molecules thus setting the stage for complement-mediated lysis and/or phagocytosis of the bacteria. The bacteria to which this invention relates can be further defined as being destroyed by phagocytic cells (if opsonized by antibody and ingested by such cells) or by direct interaction with homologous antibody and serum components such as complement wherein these mechanisms are known to be of critical importance in the elimination of such organisms. Bacterial structures such as capsules, envelopes, or slime layers which may restrict or prohibit direct "accessibility" to LPS molecules would be anticipated to decrease the utility of this invention. Examples of bacteria which contain such structures include encapsulated *Klebsiella* species and enveloped *Escherichia coli*.

Without intent to limit the scope of this invention one can identify several genuses and species of gram-negative bacteria which may be of special interest, in view of their etiological involvement in serious human disease. They broadly fall into three large families of gram-negative organisms, namely Enterobacteriaceae, Bacteroidaceae, and Pseudomonadaceae. Representative Enterobacteriaceae include for example *Escherichia coli; Klebsiella* sp. such as *K. pneumoniae, K. ozaenae*, and *K. rhinoscleromatis; Enterobacter* sp. such as *E. aerogenes, E. cloacea, E. hafniae*, and *E. agglomarans; Serratia marcescens; Proteus* sp. such as *P. vulgaris, P. mirabilis, P. rettgeri*, and *P. morganii; Provindencia stuartii;* and *Citrobacter* sp. (Sonnenwirth, supra; McCabe, supra; and Kreger et al., supra, incorporated by reference). Representative *Bacteroidaceae* include *Bacteroides* sp. such as *B. fragilis;* and *Fusobacterium* sp. (Sonnenwirth, supra, incorporated by reference). Representative *Pseudomonadaceae* include *P. aeruginosa, P. pseudomallei, P. mallei, P. fluorescens, P. putida, P. cepacia, P. strutzeri, P. maltophilia* (see Gilardi, G. L., "Pseudomonas Species in Clinical Microbiology," *Mt. Sinai J. Med.* (1976) 43:710-726, incorporated by reference). Protection against other equivalent organisms can be achieved by this invention as well.

The *Pseudomonas* species listed above represent a preferred application of the present invention, with *P. aeruginosa* being a more preferred application.

It is well known that within a particular species of gram-negative bacteria there can be a plurality of immunologically distinguishable strains or types. In many cases, differences between or among strains or types can be related to variations in the antigenic structure of LPS molecules and specifically to structural variation within the O-specific side chains of LPS molecules (see FIG. 1). Thus, structurally different O-specific side chains present different antigenic structures. Immunological recognition of such antigenic variation results in the generation of antibodies specific for a given antigenic variant. When such antibodies are used to serologically (i.e., by agglutination, ELISA, etc.) differentiate between one antigenic variant and another, the antigenic variants so recognized are termed serotypes and are said to display serotypic determinates. Thus, the *O-specific side chains of LPS molecules present serotypic antigenic determinants. It will be appreciated by those skilled in the art that since the present invention provides human monoclonal antibodies to serotypic determinants on LPS molecules, it can provide antibodies which are type specific,* meaning that they are specific to the LPS molecule of a particular type within a species.

In discussing the various serotypes, typing schemes can be usefully employed. Illustrative of such typing schemes are those of *P. aeruginosa*. The Fisher typing system of *P. aeruginosa* is well known and is described in detail in Fisher et al., "New Immunotype Scheme of *Pseudomonas aeruginosa* Based on Protective Antigens," *J. Bacteriol.* (1969) 98:835-836, which is incorported herein by reference. This system classifies the majority of known *P. aeruginosa* into seven types: Fisher immunotype 1; Fisher immunotype 2; Fisher immunotype 3; Fisher immunotype 4; Fisher immunotype 5; Fisher immunotype 6; and Fisher immunotype 7. Similarly, the International Antigenic Typing Scheme (IATS) system for *P. aeruginosa* (see, Brokopp, C. D. and Farmer, J. J., III, "Typing Methods for *Pseudomonas aeruginosa*," *Pseudomonas aeruginosa: Clinical Manifestations of Infection and Current Therapy*, pp. 89-133, Doggett, R. G., Ed., Academic Press, 1979) provides some 17 separate serotypes designed IATS type 1, IATS type 2, etc. For both the Fisher (Hanessian, S., et al., "Isolation and Characterization of Antigenic Components of a New Heptavalent *Pseudomonas* Vaccine," *Nature* (1971) 229:209-210) and the IATS typing system (Brokopp and Farmer, supra), the antigenic determinant relative to both serotypic schemes has been shown to reside on the LPS molecule. A comparison and correlation of both typing systems is presented in Table 1.

TABLE 1

| Comparison of Two *P. aeruginosa* Typing Systems | |
|---|---|
| IATS (Serotype) | Fisher (Immunotype) |
| 1 | 4 |
| 2 | 3,7 |
| 3 | — |
| 4 | — |
| 5 | 3,7 |
| 6 | 1 |
| 7 | 6 |
| 8 | 6 |
| 9 | — |
| 10 | 5 |
| 11 | 2 |
| 12 | — |
| 13 | — |
| 14 | — |
| 15 | — |
| 16 | 3,7 |
| 17 | — |

The monoclonal antibodies are produced by cell-driven Epstein-Barr virus (EBV) transformation of B lymphocyte cells obtained from human donors who are or have been exposed to the respective gram-negative bacteria. The antibody secreting cell lines so produced are characterized as continuously growing lymphoblastoid cells that possess a diploid karyotype, are Epstein-Barr nuclear antigen (EBNA) positive, and secrete monoclonal antibody of either IgG, IgM, IgA, or IgD isotype, including subtypes IgG1, IgG2, IgG3 and IgG4. The cell-driven transformation process itself is an invention of M. E. Lostrom and is described in detail in U.S. Pat. No. 4,464,465 which is incorporated herein by reference. The monoclonal antibodies may be used intact or as fragments, such as Fab, or F(ab')$_2$, usually intact. In some instances it may be desirable to conjugate the antibodies to other compounds for achieving particular results. For example, the antibodies may be conjugated to cytotoxic agents, such as radionuclides, antibiotics, etc.

This process application to produce the present monoclonal antibodies is demonstrated by the following examples. These examples are intended solely to illustrate representative embodiments of the invention and are not to be construed as limiting the invention's scope.

EXPERIMENTAL

Example I

Example I demonstrates methods for the production of a human monoclonal antibody against *P. aeruginosa* Fisher immunotype 2 (IATS type 11) LPS molecules and further demonstrates the protective activity of said antibody in vivo against a lethal challenge of the homologous strain.

A. Obtaining Suitable Human Cells

Suitable human B-cells (lymphocytes) were derived from the spleen of a deceased individual known to have harbored disease cystic fibrosis and to have had previous infections with *P. aeruginosa*. The spleen, obtained at autopsy, was cut into slices approximately 15 mm thick. Cells were liberated from the capsule and connective maxtrix into a large petri dish by gently perfusing each slice with calcium/magnesium-free phosphate buffered saline (CMF-PBS) delivered through an 18-gauge needle attached to a syringe. Mononuclear cells were separated from the splenic cell preparation by standard centrifugation techniques on Ficoll-Paque (Boyum, A., "Isolation of Mononuclear Cells and Granulocytes From Human Blood," *Scand. J. Clin. Lab. Invest.* (1968) 21:Suppl.97, 77-89) and washed twice in CMF-PBS.

The mononuclear cells were depleted of T-cells using a modified E-rosetting procedure. Briefly, the cells were first resuspended to a concentration of $1 \times 10^7$ cells/ml in PBS containing 20% fetal calf serum (FCS) at 4° C. One ml of this suspension was then placed in a $17 \times 100$ mm polystyrene round bottom tube to which was added $1 \times 10^9$ 2-amino-ethyl-isothiouronium bromide (AET)-treated sheep red blood cells from a 10% (v/v) solution in RPMI 1640 medium (Madsen, M. and Johnson, H. E., "A Methodological Study of E-rosette Formation Using AET Treated Sheep Red Blood Cells," *J. Immun. Methods* (1979) 27:61-74). The suspension was very gently mixed for 5-10 minutes at 4° C. and the E-rosetted cells then removed by centrifugation on Ficoll-Paque for 8 min at 2500 xg at 4° C. E-rosetted negative splenic mononuclear cells (E−Spl) banding at the interface were washed once in RPMI 1640 medium and resuspended in same containing 15% v/v FCS, L-glutamine (2 mmol/l), sodium pyruvate (1 mmol/l), pencillin (100 IU/ml), streptomycin (100 μg/ml), hypoxanthine ($1 \times 10^{-4}$M), aminopterin ($4 \times 10^{-7}$M), and thymidine ($1.6 \times 10^{-5}$M). This medium is hereafter referred to as HAT medium.

B. Cell-Driven Transformation of Cells

Cell-driven transformation of the E−Spl cells was accomplished by cocultivating the E−Spl cells with a transforming cell line. The transforming cell line was an Epstein-Barr nuclear antigen (EBNA) positive human lymphoblastoid cell line derived by ethylmethane sulphonate (EMS) mutagenesis of the GM 1500 lymphoblastoid cell line followed by selection in the presence of 30 µg/ml 6-thioguanine to render the cells hypoxanthine-guanine phosphoribosyl transferase (HGPRT) deficient and thus HAT sensitive. This cell line is denominated the 1A2 cell line and was deposited at the A.T.C.C. on Mar. 29, 1982, under A.T.C.C. No. CRL 8119. 1A2 cells in logarithmic growth phase were suspended in HAT medium and then combined with the E−Spl cells at a ratio of 30 1A2 cells per E−Spl cell. The cell mixture was plated into 10 flat-bottom 96 well microtiter plates at a concentration of 155,000 cells/well in a volume of 200 µl per well, and the culture incubated at 37° C. in a humidified atmosphere containing 6% $CO_2$. Cultures were fed every three to four days by replacement of half the supernatant with fresh HAT medium. The wells were observed every other day on an inverted microscope for signs of cell proliferation. Two weeks after plating the cells and after the 1A2 cells had died due to HAT selection, feeding of the wells was accomplished with a new media formulation identical to HAT media except that it lacked the aminopterin component. Eighteen days post plating, it was observed that approximately 70% of the wells contained proliferating cells and that in most of the wells, the cells were of sufficient density for removal and testing of supernatants for anti-*P. aeruginosa* antibody.

C. *Detection of Specific Antibody Secreting Cells*

Supernatants were screened for the presence of anti-*P. aeruginosa* antibodies using an enzyme linked immunosorbent assay (ELISA) technique (Engvall, E., "Quantitative Enzyme Immunoassay (ELISA) in Microbiology," *Med. Biol.* (1977) 55:193–200). The antigen plates consisted of flat-bottom 96 well microtiter plates, the wells of which contained various whole bacteria that had been ethanol-fixed to the bottom of the well. Plates were prepared by addition of 50 µl of washed bacterial suspension ($OD_{660}=0.2$) in PBS into the wells, centrifugation of the plates for 20 min at 500 xg, aspiration of PBS, addition of 75 µl of ethanol for 10 min, removal of ethanol, followd by air drying. Various antigen plates used in the screen included: (1) mixture of *P. aeruginosa* Fisher immunotypes 1 through 3 (A.T.C.C. Nos. 27312, 27313, 27314); (2) a mixture of *P. aeruginosa* Fisher immunotypes 4 through 7 (A.T.C.C. Nos. 27315, 27316, 27317, 27318); (3) a clinical isolate of *Escherichia coli*; (4) *Klebsiella pneumoniae* (A.T.C.C. No. 8047); and (5) a microtiter plate with no bacteria.

For the ELISA procedure, wells of the antigen plates were first blocked with 75 µl of 5% BSA for 1 hr to prevent non-specific binding of protein. After flicking out unadsorbed BSA, supernatants from wells of the culture plate were replica plated into the corresponding wells of the antigen plates (50 µl/well) and the plates incubated at 37° C. in a humidified chamber for 30 min. The supernatants were then removed, the wells washed 3 times with 1% BSA-PBS, and 50 µl of biotinylated goat anti-human immunoglobulin (Ig) (Tago #2593 diluted 1:1000 in 1% BSA-PBS) added to each well. After a 30 min incubation at 37° C. in a humidified chamber, the biotinylated anti-human Ig was removed, the wells washed 3 times with 1% BSA-PBS, and 50 µl of a preformed avidin:biotinylated horseradish peroxidase complex (Vectastain ABC Kit, Vector Laboratories, Inc., Burlingame, CA) added to each well. After a 30 min incubation at room temperature, the excess Vectastain ABC reagent was removed, the wells again washed 3 times with 1% BSA-PBS, and 100 µl of substrate (0.8 mg/ml ortho-phenylenediamine dihydrochloride in 100 mM citrate buffer, pH 5.0, plus 0.03% $H_2O_2$ in deionized $H_2O$, mixed in equal volumes just before plating) added to each well. After a 30 min incubation in the dark, 50 µl of 3N $H_2SO_4$ was added to each well to terminate reactions. Culture supernatants containing antibodies corresponding to the plate's antigen were detected by positive color development in the corresponding wells and the strength of the reaction quantitated by measuring the absorbence at 490 nm on a Dynatech MR 580 micro ELISA reader.

Analysis of the culture supernatants by the above method led to the identification of three wells (6F11, 4G9, and 10B2) which contained anti-*P. aeruginosa* specificity on the Fisher immunotypes 1 through 3 plate but not the Fisher immunotypes 4 through 7 plate or any of the control plates. In order to identify the specific Fisher immunotype recognized, antigen plates containing ethanol-fixed bacteria of only one Fisher immunotype were prepared as described above for each immunotype. Performance of the ELISA assay as set forth above with culture supernatants from wells 6F11, 4G9 and 10B2 on the individual immunotype plates indicated that these three wells contained antibody specific to the Fisher 2 immunotype.

D. Cloning of Specific Antibody Producing Cells

The cells in wells 6F11, 4G9, and 10B2 were subjected to several rounds of cloning (two or three) until all clonal supernatants assayed by the above ELISA procedure on Fisher 2 immunotype antigen plates gave a positive reaction. Cells were cloned by limiting dilution on a semi-confluent layer of human foreskin fibroblasts in flat-bottom 96 well plates. Media consisted of RPMI 1640 containing 15% v/v FCS, L-glutamine (2 mmol/l), sodium pyruvate (1 mmol/l), pencillin (100 IU/ml), and streptomycin (100 µg/ml). Cultures were fed every 3 days by replacement of half the supernatant with fresh media. In general, wells were of sufficient lymphoblastoid cell density between 2 and 3 weeks post-plating for analysis of anti-Fisher 2 immunotype specificity.

Thus, in this experiment three cloned transformed human cell lines were achieved which are continuous (immortal) and which each secrete human monoclonal antibodies to serotypic determinants on the LPS molecules of Fisher immunotype 2 *P. aeruginosa*. In this and subsequent examples the cell line and antibody it produces carry the same designation.

Prior to the filing of this patent application, the continuous transformed human cell line identified herein as 6F11 was deposited in the American Type Culture Collection, Rockville, MD, as A.T.C.C. No. CRL 8562.

E. Characterization of Monoclonal Antibodies

The fact that the monoclonal antibodies from each of the clones reacted exclusively with a single (in this case Fisher 2) immunotype suggested the antibody was directed against a lipopolysaccharide antigen since LPS serotype correlates with the Fisher immunotyping system (Hanessian, *Nature* (New Biology) (1971)

229:209–210). To examine this further, an expanded ELISA test was performed with the 6F11, 4G9, and 10B2 supernatants on whole fixed bacteria plates that contained the seventeen IATS serotype strains of *P. aeruginosa*, *P. aureofaciens*, the J5 mutant of *E. coli* 0111:B4 and a clinical isolate of *Providencia stuartii*. In complete agreement with a comparison of the Fisher immunotypes and their corresponding LPS-based serotypes in the IATS scheme (see Table 1), each of the anti-Fisher immunotype 2 clonal supernatants was reactive with only IATS strain 11. No reactions were observed on any of the non-*P. aeruginosa* bacteria.

One of the three human anti-Fisher immunotype 2 monoclonal antibodies was further characterized. Based on stronger reactivity of the antibody in ELISAs and better growth properties of the respective cell line, the 6F11 monoclonal was chosen.

Biochemical characterization of the molecular species recognized by the 6F11 antibody was accomplished by immunoblot analysis. Briefly, 20 $\mu$g of crude LPS (prepared by the hot phenol-water method (Westphal, O., et al., "Uber die Extraktion von Bakterien mit Phenol/Wasser," *Z. Naturforsch* (1952) 79:148–155) from each of the seven Fisher immunotypes, 20 $\mu$g of chromatographically purified LPS from *E. coli* 0111:B4 and *Klebsiella pneumoniae* (both from List Laboratories, Campbell CA), and 50 $\mu$g of an outer membrane preparation (Tam, M. R., et al., "Serological Classification of *Neisseria gonorrhoeae* With Monoclonal Antibodies," *Infect. Immun.* (1982) 36:1042–1053) of Fisher immunotype 2 bacteria were each subjected to sodium dodecyl sulphate (SDS)-polyacrylamide gel electrophoresis (Hancock, R. E. W. and Carey, A. M., "Outer Membrane of *Pseudomonas aeruginosa*: Heat and 2-Mercaptoethanol-Modifiable Proteins," *J. Bacteriol.* (1977) 140:901–910). Separated molecular species were transferred from the gel to a nitrocellulose membrane (NCM) as described elsewhere (Towbin, H., et al., "Electrophoretic Transfer of Proteins From Polyacrylamide Gels to Nitrocellulose Sheets: Procedure and Some Applications," *Proc. Natl. Acad. Sci. USA* (1979) 76:4350–4354) and the NCM blot blocked for 1 hr in PBS-Tween (Batteiger, B., et al., "The Use of Tween 20 as a Blocking Agent in the Immunological Detection of Proteins Transferred to Nitrocellulose Membranes," *J. Immunol. Meth.* (1982) 55:297–307). The blot was then incubated for 1 hr at room temperature (RT) in 30 ml PBS-Tween containing 3 ml of spent culture supernatant from the 6F11 line. Following four 5 min rinses in PBS-Tween, the blot was incubated in a 1:5000 dilution (in PBS-Tween) of rabbit anti-human Ig for 1 hr at RT. The blot was rinsed four times in PBS-Tween and then placed in 30 ml of a solution containing a 1:2000 dilution (in PBS-Tween) of protein A-horseradish peroxidase (Zymed Laboratories Inc., San Francisco, CA). After an hour incubation at RT the blot was rinsed four times in PBS-Tween and then submerged in 60 ml of substrate prepared as follows: 120 mg of horseradish peroxidase-color development reagent (Bio-Rad Laboratories, Richmond, CA) was dissolved in 40 ml cold methanol; 120 $\mu$l of 30% $H_2O_2$ was added to 200 ml Tris-Buffered Saline (TBS-20 mM Tris pH 7.4, 0.5M NaCl); the two solutions were mixed just prior to addition to blots. After appropriate color development (usually 15 to 45 min after addition of substrate) the reaction was quenched by rinsing the blot several times in deionized water.

Results were as follows. Positive reactions were noted only in the tracks that contained Fisher immunotype 2 crude LPS and the outer membrane preparation of Fisher immunotype 2 bacteria. In both of these tracks, the 6F11 antibody appeared to recognize a series of regularly spaced molecular entities giving rise to a ladder-like pattern on the immunoblot. This profile was entirely consistent with that seen in polyacrylamide gel electrophoretic analysis of LPS in the presence of SDS, where it has been demonstrated that the heterogeneous size profile exhibited by the bands is due to a population of LPS molecules differing by weight increments equivalent to the number of O-antigenic oligosaccharide side chain units present per molecule. (Pavla, E. T. and Makela, P. H., "Lipopolysaccharide Heterogeneity in *Salmonella typhimurium* Analyzed by Sodium Dodecyl Sulfate/Polyacrylamide Gel Electrophoresis," *Eur. J. Biochem.*, (1980) 107:137–143; and Goldman, R. D. and Leive, L., "Heterogeneity of Antigenic-Side-Chain Length in Lipopolysaccharide from *Escherichia coli* 0111 and *Salmonella typhimurium* LT2, *Eur. J. Biochem.* (1980) 107:145–153). Collectively, these data indicate that the serological specificity of monoclonal antibody 6F11 is directed against the LPS molecule on the Fisher immunotype 2 bacteria. Furthermore, since serological specificity of LPS molecules is based on the structure of the repeating oligosaccharide units and/or their glycosidic linkages (Westphal et al., *Prog. Allergy* (1983) 33:9–39), the data demonstrate that monoclonal antibody 6F11 is specific for some part of the oligosaccharide unit or the linkage between such units rather than serologically conserved structures of LPS represented by the core region and lipid A.

The isotype of the 6F11 monoclonal antibody was determined in an ELISA assay similar to the specificity tests described earlier except that biotinylated goat anti-human IgG (gamma-chain specific, Tago) or biotinylated goat anti-human IgM (mu-chain specific, Tago) was used as the second step reagent instead of the more broadly reactive biotinylated goat anti-human Ig. Both reagents were used at a 1:500 dilution and the antigen plate contained ethanol fixed Fisher immunotype 2 bacteria. Positive reaction of the 6F11 antibody with Fisher immunotype 2 bacteria was observed only with the anti-IgM reagent, demonstrating an IgM isotype for the monoclonal antibody.

F. In Vitro Activity

In vitro functional activity of the 6F11 monoclonal antibody was examined in an opsonophagocytic assay which compared the uptake of radiolabeled bacteria by human neutrophils in the presence of complement when the 6F11 monoclonal antibody was present and not present.

Radiolabeled bacteria were prepared by inoculating 5 ml of Pseudomonas minimal media (Auerard and Snell, Chapter 7, "Biochemical Factors in Growth," *Manual of Methods for General Bacteriology*, Gerhardt, P. et al., eds, American Society for Microbiology, Washington, D.C. 1981, pp. 79–111) with 100 $\mu$l (1 $\mu$Ci) of $^3$H-leucine (146.5 Ci/mmol, New England Nuclear, Boston, MA) and 30 $\mu$l of an overnight trypticase soy broth culture of Fisher immunotype 2 P. aeruginosa. The tube was incubated at 37° C. on a shaker for 4–6 hr after which the excess $^3$H-leucine was removed by four washes in Hank's balanced saline solution containing 0.1% gelatin and 5 mM HEPES, (HBSS/Gel), pH 7.2 Bacteria were centrifuged at 950 xg for 10 min for each wash and resuspended in HBSS/Gel to a final concentration of 6.67×10⁶/ml. Human neutrophils were isolated according to van Furth and Van Zwet ("In Vitro Determination of Phagocytosis and Intracellular Killing by Polymorphonuclear and Mononuclear Phagocytes," in *Handbook of Experimental Immunology* (1973) Vol. 2, D. M. Weir, ed., 2nd edition, Blackwell Scientific Publications, Oxford, 36.1-36.24) with several modifications. Buffy coat from 10 mls of heparinized blood was underlayed with Ficoll-Paque and centrifuged. The red blood cell (RBC) pellet was washed once in RPMI 1640 medium and resuspended in an equal volume of 37° C. PBS. Three mls of this suspension was then added to 6 mls of 2% dextran (in 37° C. PBS) and the contents gently but thoroughly mixed end over end. After a 20 min incubation at 37° C. to allow the RBCs to sediment, the supernatant (containing neutrophils) was removed and washed twice in 4° C. PBS. Cells were washed once more in 4° C. HBSS-HEPES (pH 7.2) and resuspended in same to $5 \times 10^7$ neutrophils/ml. Lyophilized rabbit serum reconstituted in 0.01M EDTA (pH 7.2) and twice absorbed with live bacteria (Bjornson, A. B. and Michael, J.G., "Factors in Human Serum Promoting Phagocytosis of *Pseudomonas aeruginosa*. I. Interaction of Opsonins With the Bacterium," *J. Inf. Dis.* (1974) 130:Suppl.S119-S125) representing the seven Fisher immunotypes, served as a source of complement.

For the assay, 300 μl of Fisher immunotype 2 bacterial suspension was added to 100 μl of 6F11 culture supernatant (diluted 1:1 with heat inactivated FCS) in a 1.5 ml Eppendorf tube and incubated on a rotator at 37° C. for 30 min. This was followed by the sequential addition of 50 μl of complement and then 50 μl of neutrophil suspension with 30 min and 45 min incubation periods on a rotator at 37° C. after each of the respective additions. The neutrophils were then washed twice by filling the tube with cold PBS, centrifuging for 5 min at 100 xg and removing the supernatant. 250 μl of 0.1N NaOH was added to lyse the neutrophils, the tube incubated for 15 min, vortexed, and incubated another 15 min at which time 250 μl of the tube's contents was solubilized in 3 ml of scintillation fluid (Dimilume 30, United Technologies, Packard) and counted using a Beckman LS 7000 liquid scintillation counter. Results were expressed as percent uptake of input radiolabeled bacteria. Cpm associated with input radiolabeled bacteria were measured by counting 250 μl of a control tube's contents which had been subjected to the above procedure except for the addition of heat inactivated (56° C., 30 min) normal rabbit serum for monoclonal antibody and no washes to remove uningested bacteria.

As shown in Table 2, Fisher immunotype 2 bacteria was phagocytosed only in the presence of monoclonal antibody 6F11 and an active source of complement. When this experiment was repeated using Fisher immunotype 1 bacteria instead of Fisher immunotype 2 bacteria, no bacterial uptake was observed thus demonstrating the specificity of 6F11 antibody's capacity to opsonize bacteria and promote phagocytosis. Since the combined action of opsonins (specific antibodies) and polymorphonuclear leukocytes (neutrophils) appears to be the primary mechanism of immunity to *P. aeruginosa* (Pollack, supra), these data suggest that antibody 6F11 would, under appropriate administration, provide protection against a lethal challenge of Fisher immunotype 2 bacteria.

TABLE 2

| 6F11 Antibody[a] | Complement[b] | Percent Uptake of Input ³H-Fisher Immunotype 2 Bacteria |
|---|---|---|
| − | − | 3.8 |
| + | − | 6.6 |
| − | + | 2.4 |
| + | + | 61.7 |

[a](−) = culture media
[b](−) = heat inactivated complement

G. In Vivo Activity

To test the above hypothesis, animal protection studies were performed with the 6F11 antibody and several Fisher immunotypes of *P. aeruginosa*. 6F11 antibody was first concentrated from spent culture supernatant by precipitation with saturated ammonium sulphate (50% final concentration) (Good, A. H., et al., "Purification of Immunoglobulins and Their Fragments," *Selected Methods in Cellular Immunology*, Mishell, B. B. and Shiigi, S M., eds., W. H. Freeman & Co., San Francisco, CA, 279-286 (1980)). Precipitated material was reconstituted in sterile water, extensively dialyzed against PBS, and sterile filtered. Fresh culture media subjected to the same procedure served as a negative control. Female BALB/c mice between 20 and 22 gm body weight were divided into two groups of ten mice each. One group was inoculated intraperitoneally (ip) with 0.5 ml of concentrated 6F11 antibody (containing approximately 50 μg antibody as determined by radioimmune assay) while the other group received ip 0.5 ml of concentrated culture media. Six hours later, all animals were challenged ip with 0.3 ml of a live bacterial suspension containing 5LD₅₀ of Fisher immunotype 2 *P. aeruginosa*. *The bacterial suspension had been prepared from a broth culture in logarithmic phase growth, from which the bacteria were centrifuged, washed twice in PBS and resuspended to the appropriate density in PBS. The bacterial challenge represented $1.2 \times 10^8$ live organisms.* Animals were observed for a period of five days. Eighteen hours post challenge, all the animals that had received concentrated culture media were dead. In contrast, those animals that had received 6F11 monoclonal antibody were all alive. The latter group appeared quite healthy at this point with only minor symptoms of bacterial infection (i.e., a slight ruffling of the fur). These symptoms disappeared by 48 hr post challenge with no further evidence of bacterial disease during the remainder of the observation period. Similar experiments performed using a challenge of 5LD₅₀ of other Fisher immunotypes of *P. aeruginosa* resulted in no protection by the 6F11 antibody. These data clearly demonstrate that passively transferred 6F11 antibody provides complete and specific protection against a lethal challenge dose of *P. aeruginosa*.

Example II

Example II demonstrates a method for the production of a human monoclonal antibody against *P. aeruginosa* Fisher immunotype 4.

Peripheral blood lymphocytes (PBL) from a human with previous exposure to *P. aeruginosa* were employed. Ten plates were seeded with 2000 E³¹ PBL/well plus 40,000 1A2 cells/well in Iscove's modified Dulbecco's medium supplemented to 15% (v/v) FCS, L-glutamine (2 mmol/l), penicillin (100 IU/ml), streptomycin (100 μg/ml) and HAT as described in Example I. This media formulation is hereafter referred to as Iscove's medium.

The assay procedure described in Example I was employed, except the *E. coli* and *K. pneumoniae* assay plates were deleted. A supernatant in one of the wells, designated 9D10, was positive only on the Fisher immunotype 4–7 plate and was subsequently determined to be Fisher 4 specific when assayed on individual immunotype antigen plates. Cloning of cells from well 9D10 was performed using irradiated human PBL ($2.5 \times 10^5$/well) as feeder cells in 0.5-area 96-well flat-bottom plates, and Iscove's medium without the HAT supplement, but the procedure is otherwise as described previously. Prior to filing of this patent application, cell line 9D10 described herein was deposited in the American Type Culture Collection and given the designation CRL 8752.

The antibody 9D10 was characterized as IgM in an isotype determination as described previously and was shown to react only with IATS strain 1 in a specificity test on IATS serotypes. Employing previously described procedures for immunoblot analysis, the subject antibody reacted only with Fisher immunotype 4 LPS and an outer membrane preparation from Fisher immunotype 4 bacteria, demonstrating a ladder-like profile similar to that described for the 6F11 antibody.

Employing the previous procedures for in vitro and in vivo activity, the following results were obtained.

TABLE 3

| | Opsonophagocytic Assay: | |
|---|---|---|
| 9D10 Antibody[a] | Complement[b] | % Uptake of Input $^3$H-Fisher Immunotype 4 Bacteria |
| − | − | 8.4 |
| + | − | 4.9 |
| − | + | 9.5 |
| + | + | 65.3 |

[a](−) = culture media
[b](−) = heat inactivated complement
For in vivo data see Table on page 27 relating to 9D10 antibody.

Example III

Example III demonstrates a method for the production of human monoclonal antibodies against *P. aeruginosa* Fisher immunotypes 1 and 4.

The lymphocyte source employed was from a cystic fibrosis patient whose serum contained above normal titers to the LPS of several Fisher immunotypes. In this instance five plates were seeded at 15,000 PBL/well plus 140,000 1A2 cells/well. The same Iscove's media formulation was employed as described in Example II, but was supplemented with 0.5 µg/ml cyclosporin A for the purpose of functionally inactivating T-cells. There was no T-cell depletion through rosetting with AET-SRBC used in this experiment. The cyclosporin A presence was maintained in media until the assay of master wells.

Screening of the culture supernatants was performed as described in Example II. A supernatant from the well designated C5D5 was positive only on the Fisher immunotypes 4–7 plate and was confirmed as Fisher immunotype 4 specific on individual immunotype antigen plates as described previously. Another supernatant from the well designated C5B7 reacted only on the Fisher immunotypes 1–3 plate and was confirmed as specific for Fisher immunotype 1 on individual immunotype antigen plates as described previously. Prior to filing of this patent application, cell lines C5B7 and C5D5 were deposited in the American Type Culture Collection and given the designation CRL 8753 and CRL 8754, respectively. Both C5D5 and C5B7 were shown to be IgM as determined by isotype analysis as described previously. C5D5 reacted only with IATS strain 1, while C5B7 reacted only with IATS strain 6 as expected from the relationship between Fisher immunotypes and IATS serotypes.

In immunoblot analysis, the subject antibody C5D5 was shown to react only with Fisher immunotype 4 LPS and an outer membrane preparation from Fisher immunotype 4 bacteria exhibiting a ladder-like profile similar to that described for the 6F11 antibody.

In a similar immunoblot analysis, the antibody C5B7 reacted only with Fisher immunotype 1 LPS and an outer membrane preparation of a Fisher immunotype 1 strain exhibiting a ladder-like profile.

In vitro and in vivo assays as described previously provided the following results.

| | Opsonophagocytic Assay: | |
|---|---|---|
| C5D5 Antibody[a] | Complement[b] | % Uptake of Input $^3$H-Fisher Immunotype 4 Bacteria |
| − | − | 8.4 |
| + | − | 6.3 |
| − | + | 9.5 |
| + | + | 56.1 |

| C5B7 Antibody[a] | Complement[b] | % Uptake of Input $^3$H-Fisher Immunotype 1 Bacteria |
|---|---|---|
| − | − | 6.3 |
| + | − | 6.9 |
| − | + | 17.7 |
| + | + | 56.3 |

| In Vivo Protection Studies: | |
|---|---|
| | # live/total 3 days post challenge |
| C5D5 & 9D10 | |
| Media | 0/10 |
| C5D5 (Anti-Fisher 4) | 10/10 |
| C5B7 (Anti-Fisher 1) | 1/10 |
| 9D10 (Anti-Fisher 4) | 8/10 |
| No further changes after 3 days. | |
| Challenge dose: 5 LD$_{50}$ live Fisher immunotype 4 bacteria. | |
| C5B7 | |
| Media | 0/10 |
| C5D5 (Anti-Fisher 4) | 2/10 |
| 9D10 (Anti-Fisher 4) | 0/10 |
| C5B7 (Anti-Fisher 1) | 8/10 |
| No further changes after 3 days. | |
| Challenge dose: 5 LD$_{50}$ live Fisher immunotype 1 bacteria. | |

[a](−) = culture media
[b](−) = heat inactivated complement

Example IV

Example IV demonstrates a method for the production of human monoclonal antibodies against *P. aeruginosa* Fisher immunotypes 5 and 6 and further demonstrates the protective activity of said antibodies in vivo against a lethal challenge of the homologous strain.

A peripheral blood sample was obtained from a cystic fibrosis patient known to have had chronic infection with *P. aeruginosa*. Mononuclear cells were separated from the blood as described in Example I. Cell-driven transformation of susceptible B cells was performed as described in Example III except that 23 plates were seeded at 20,000 mononuclear cells plus 80,000 1A2 cells per well in round-bottom 96-well plates (Costar 3799).

Sreening of the culture supernatants for specific antibodies was performed using a modification of the ELISA assay described in Example I. Antigen plates consisted of flat-bottom 96-well microtiter plates (Immulon II, Dynatech), the wells of which contained various live bacteria adsorbed to the bottom of the well. To facilitate adsorption of the bacteria to the plastic, 50 μl/well of poly-L-lysin (PLL) (1 μg/ml in PBS, pH 7.2) was incubated for 30 min at room temperature. The unadsorbed PLL was then flicked out, the plates washed once with PBS, 50 μl of washed bacterial suspension ($OD_{660}$=0.2) in PBS added to each well, and the plates incubated for 1 hr at 37° C. Unadsorbed bacteria was removed by washing the plates three times with saline-Tween [0.9% NaCl, 0.05% (v/v) Tween-20]. Bacterial composition of the plates was as described in Example I except that no *E. coli* or *K. pneumoniae* plates were employed. The ELISA was initiated by first blocking the plates with 200 μl/well of blocking butter [PBS, pH 7.2, containing 5% (w/v) non-fat dry milk, 0.01% (v/v) Antifoam A (Sigma), and 0.01% (w/v) thimerosal] for 60 min at room temperature. After blocking, the plates were washed three times with saline-Tween. Fifty μl of PBS, pH 7.2, containing 0.1% Tween-20 and 0.2% (w/v) BSA was then placed in all wells. Supernatants from wells of culture plates were replica plated into the corresponding wells of the antigen plates (50 μl/well) and the plates were incubated 30 min at room temperature. Supernatants were then removed, the wells washed three times with saline-Tween, and 50 μl of appropriately diluted horseradish peroxidase (HRP) conjugated goat anti-human IgG+IgM (American Qualex International #A1114-+#A1124) was added to the wells. In this example, HRP-goat anti-IgG and HRP-goat anti-IgM were used at a final dilution of 1.5000 and 1:3000, respectively, in PBS, pH 7.2, containing 0.05% Tween-20 and 0.1% BSA. Following a 30 min incubation at room temperature, excess enzyme conjugated goat antibodies were removed and the wells washed three times with saline-Tween. The remainder of the ELISA involving addition of substrate and subsequent color development was performed as described in Example I.

Analysis of the culture supernatants by the above method led to the identification of two wells (13C1 and 5G2) that were positive only on the Fisher immunotypes 4-7 plates. It was subsequently determined by ELISA on individual immunotype antigen plates that the antibody in well 13C1 was Fisher immunotype 5 specific whereas the antibody in well 5G2 was Fisher immunotype 6 specific. Isotype determination as described in Example I but utilizing the ELISA format and HRP-anti-human IgG and HRP-anti-human IgM reagents described in the current example, demonstrated an IgM isotype for each of the above Fisher immunotype specific antibodies.

Cloning of specific antibody-producing cells from wells 13C1 and 5G2 was accomplished by independently subjecting the cells from each well to several rounds of limiting dilution cloning until all clonal supernatants assayed by the above ELISA protocol resulted in a positive reaction on the appropriate Fisher immunotye. Cloning was performed in 96-well round-bottom plates with $1 \times 10^5$ irradiated (2400 Rads) human PBLs per well as feeder cells. Seven days later, an additional $1 \times 10^5$ irradiated PBLs were added to each well.

The resulting clonal cell line producing anti-Fisher immunotype 5 human monoclonal antibody is designated 13C1 whereas the clonal cell line producing anti-Fisher immunotype 6 human monoclonal antibody is designated 5G2. The monoclonal antibody produced by each of the clonal lines carries the same designation as the respective line that produces it.

Prior to filing of this patent application, cell lines 13C1 and 5G2 described herein were deposited in the American Type Culture Collection and given the designations CRL 8796 and CRL 8797, respectively.

Immunoblot analysis was performed on outer membrane preparations (OMP) from each of the seven Fisher immunotypes with monoclonal antibodies 13C1 and 5G2 described in Example I with the following modifications. Following incubation with monoclonal antibody and the subsequent wash series in PBS-Tween, each of the NCM blots was incubated for 1 hr at 25° C. in a 1:1000 dilution (in PBS-Tween) of alkaline phosphatase conjugated goat anti-human IgG+IgA+IgM (Zymed). The blots were then subjected to five 5 min washes in PBS-Tween at which time antigen-antibody interactions were visualized by incubating the blots for 20-30 min at 25° C. in 30 ml of nitrobluetetrazolium/5-bromo-4-chloro-3-indolyl phosphate (NBT-BCIP) substrate as described by Leary et al., *Proc. Natl. Acad. Sci. USA* (1983) 80:4045-4049. Color development was stopped by rinsing the blot several times in deionized water. Monoclonal antibodies 13C1 and 5G2 demonstrated a positive reaction only in those cases of homologous antibody:bacterial outer membrane combinations. That is, monoclonal antibody 13C1 reacted only with the OMP from Fisher immunotype 5 and monoclonal antibody 5G2 reacted only with the OMP from Fisher immunotype 6. In both cases the reaction resulted in a ladder-like profile of regularly spaced bands indicative of LPS as the recognized molecular target. In support of LPS as the target antigen, it was further noted that the ladder-like profiles were unaltered in each case when the OMPs were heat treated (100° C., 1 hr) and then incubated at 60° C. for 2 hr in the presence of proteinase K (10-20 μg/50 μg protein in sample) prior to electrophoresis. The latter pre-treatments are known to be destructive for protein antigens.

In vitro functional activity of human monoclonal antibodies 13C1 and 5C2 was examined in an opsonophagocytic bactericidal assay. Bacteria were harvested in log phase growth from culture in trypticase soy broth, resuspended to an $OD_{660}$=0.100 in Hank's balanced saline solution containing 0.1% gelatin and 5mM HEPES (HBSS/GEL/HEPES), and then diluted 1:1000 in the same buffer. Human neutrophils were isolated from the blood of normal volunteers as described in Example I and resuspended to $5 \times 10^7$ neutrophils/ml in HBSS/GEL/HEPES. Serum from clotted blood of normal volunteers served as a source of human complement. Prior to use, nine parts of serum was combined with 1 part 0.1M EDTA, pH 7.2, and then absorbed with the seven Fisher immunotypes of *P. aeruginosa* as detailed in Example I. To prevent activation of alternative pathway complement components, the absorbed serum was further treated with Zymosan (Sigma) to remove properdin as described in Bjornson and Michael, *J. Inf. Dis.* (1974) 130 Suppl.: S119-125.

Reactions were initiated in 1.5 ml polypropylene conical tubes by combining 100 μl of bacterial suspension and 50 μl of monoclonal antibody containing supernatant. After a 30 min incubation at room temperature, 50 μl of complement, 50 μl of neutrophil suspension, and 250 μl of HBSS/GEL/HEPES were added to each tube. Tubes were incubated for another hour at 37° C. on a rotator after which 10 μl from each tube was mixed with 3 ml of liquid trypticase soy agar (45° C.) and the contents poured onto trypticase soy agar plates. After allowing sufficient time for the agar to solidify, the plates were overlayed with another 3 mls of liquid trypticase soy agar. Plates were incubated overnight at 37° C. and resulting bacterial colonies counted the next day on a Quebec colony counter. Appropriate controls to examine antibody specificity and whether or not bactericidal activity was the result of opsonophagocytosis, were assessed by (1) the addition of inappropriate monoclonal antibody instead of appropriate antibody, and (2) replacement of neutrophils with HBSS/GEL/HEPES respectively. As shown in the tables below, monoclonal antibodies 13C1 and 5G2 were bactericidal with respect to their homologous strains. In each case, the results indicate that phagocytic uptake of opsonized bacteria by human neutrophils was primarily responsible for reduction of bacterial counts. Repetition of these experiments using non-homologous antibody-bacteria combinations resulted in no bacterial uptake thus demonstrating the functional specificity of each of the above antibodies as opsonic antibodies.

| Opsonophagocytic Bactericidal Assay: | | |
| --- | --- | --- |
| 13C1 Antibody[a] | Neutrophils[b] | Number of Bacterial Colonies[c] |
| − | − | 844 |
| + | − | 721 |
| − | + | 756 |
| + | + | 11 |

[a](−) = Human anti-Fisher immunotype 2 monoclonal antibody 6F11
[b](−) = HBSS/GEL/HEPES only
[c]Experiment performed on Fisher immunotype 5 bacteria

| 5G2 Antibody[a] | Neutrophils[b] | Number of Bacterial Colonies[c] |
| --- | --- | --- |
| − | − | 451 |
| + | − | 422 |
| − | + | 570 |
| + | + | 166 |

[a](−) = Human anti-Fisher immunotype 2 monoclonal antibody 6F11
[b](−) = HBSS/GEL/HEPES only
[c]Experiment performed on Fisher immunotype 6 bacteria Employing the procedures detailed in Example I for the assessment of in vivo activity of the monoclonal antibodies, the following results were obtained and clearly demonstrated that antibodies 13C1 and 5G2 provide protection against a lethal challenge dose of the homologous strain.

| In Vivo Protection Studies: | |
| --- | --- |
| | # live/total 3 days post challenge |
| 13C1 | |
| 13C1 (Anti-Fisher 5) | 10/10 |
| C5B7 (Anti-Fisher 1) | 0/10 |
| No further changes after 3 days | |
| Challenge dose: 5 LD$_{50}$ live Fisher immunotype 5 bacteria | |
| 5G2 | |
| 5G2 (Anti-Fisher 6) | 10/10 |
| C5B7 (Anti-Fisher 1) | 0/10 |
| No further changes after 3 days | |
| Challenge dose: 5 LD$_{50}$ live Fisher immunotype 6 bacteria | |

Example V

Example V demonstrates a method for production of a human monoclonal antibody against *P. aeruginosa* Fisher immunotype 7 and further demonstrates the protective activity of said antibody in vivo against a lethal challenge of the homologous strain.

A peripheral blood sample was obtained from a cystic fibrosis patient known to have had chronic infection with *P. aeruginosa*. Mononuclear cells were separated from the blood as described in Example I. Cell-driven transformation of susceptible B cells was performed as described in Example II except that eight plates were seeded at 8000 E−PBLS plus 60,000 1A2 cells per well in round-bottom 96-well plates.

Screening of the culture supernatants for specific antibodies was performed as described in Example IV. A supernatant in one of the wells designated 8E7 was positive only on the Fisher immunotypes 4–7 plate and was subsequently determined to be Fisher 7 specific when assayed on individual immunotype antigen plates. Isotype determination as described in Example IV demonstrated an IgM isotype for the Fisher immunotype 7 specific antibody.

Cloning of specific antibody-producing cells of well 8E7 was accomplished following the protocol described in Example IV. The resulting clonal cell line producing anti-Fisher immunotype 7 human monoclonal antibody is designated 8E7. The monoclonal antibody produced by this line carries the same designation. Prior to filing of this patent application, cell line 8E7 described herein was deposited in the American Type Culture Collection and given the designation CRL 8795.

Immunoblot analysis conducted as described in Example IV on outer membrane preparations (OMP) from each of the seven Fisher immunotypes with monoclonal antibody 8E7 demonstrated a positive reaction only on the OMP from Fisher immunotype 7. The reaction resulted in a ladder-like profile of regularly spaced bands indicative of LPS as the recognized molecular target. The immunoblot profile was unaltered when Fisher immunotype 7 OMP was heated and proteinase K treated (see Example IV) prior to electrophoresis, further supporting LPS as the target antigen.

Employing procedures detailed in Example I for the assessment in vivo activity of monoclonal antibody 8E7, the following results were obtained and clearly demonstrate that antibody 8E7 provides protection against a lethal challenge dose of Fisher immunotype 7 bacteria.

| In Vivo Protection Studies: | |
| --- | --- |
| 8E7 | # live/total 3 days post challenge |
| 8E7 (Anti-Fisher 7) | 10/10 |
| C5B7 (Anti-Fisher 1) | 1/10 |
| No further changes after 3 days | |
| Challenge dose: 5 LD$_{50}$ live Fisher immunotype 7 bacteria | |

Example VI

Example VI demonstrates methods for the production of human monoclonal antibodies against serotypic determinants on the LPS molecules of species of *Pseudomonas* other than *P. aeruginosa*. It further demonstrates methods for selecting from human monoclonal antibodies so produced, those that are protective in mammals against a lethal challenge dose of the homologous bacteria.

The processes of Examples I–IV can be repeated using as starting material lymphocytes harvested from human donors exposed to other species of *Pseudomonas*, for example, *P. mallei, P. pseudomallei, P. fluorescens, P. putida, P. cepacia, P. stutzeri,* and *P. maltophilia*. Potential donors can be screened as set forth in Example IV to determine persons exposed to the various Pseudomonas species and subtypes within such species. Carrying out the processes of Examples I–IV would give rise to immortal human cell lines secreting type-specific human monoclonal antibodies against the LPS molecules of individual types of these species of Pseudomonas. Further analysis of these monoclonal antibodies in accordance with Examples I–IV, would identify those antibodies which are protective against the lethal consequence of infection due to the homologous strain.

Example VII

Example VII demonstrates methods for the production of human monoclonal antibodies against serotypic determinants on the LPS molecules of strains of gram-negative bacteria other than the genus Pseudomonas. It further demonstrates methods for selecting from human monoclonal antibodies so produced, those that are protective in mammals against a lethal challenge dose of the homologous bacteria.

The processes of Examples I–IV can be repeated using as starting material lymphocytes harvested from human donors exposed to other strains of gram-negative bacteria such as *E. coli, K. pneumoniae, P. vulgaris* and *S. marcescens*. Potential donors can be screened to identify persons previously exposed to various strains of such bacteria. Performance of procedures as previously described would result in immortal human cell lines secreting human monoclonal antibodies against serotypic determinants on the LPS molecules of *E. coli, K. pneumoniae, P. vulgaris* and *S. marcescens, respectively. Analysis of these human monoclonal antibodies as previously described would denote which antibodies are protective against the lethal consequences of infection due to the homologous strain provided that the targeted LPS molecules of the homologous strain are "accessible" (see discussion of "accessibility" of LPS molecules, supra).*

Pharmaceutical Formulations and Use

The monoclonal antibodies of this invention can be incorporated as components of pharmaceutical compositions containing a therapeutic or prophylactic amount of at least one of the monoclonal antibodies of this invention with a pharmaceutically effective carrier. A pharmaceutical carrier should be any compatible, non-toxic substance suitable to deliver the monoclonal antibodies to the patient. Sterile water, alcohol, fats, waxes, and inert solids may be used as the carrier. Pharmaceutically accepted adjuvants (buffering agents, dispersing agents) may also be incorporated into the pharmaceutical composition. Such compositions can contain a single monoclonal antibody so as to be specific against one particular strain or type of bacteria. This offers the advantage of being an exquisitely specific material containing no extraneous antibodies. Such a product may have a disadvantage as well in that it is so specific that it does not have broad application. Alternatively, a pharmaceutical composition can contain two or more monoclonal antibodies to form a "cocktail." For example, with *P. aeruginosa*, a cocktail containing human monoclonal anitbodies against each of the immunotypes or serotypes would be a universal product with activity against the great majority of the common types of that particular bacterium. With other species and strains, a single antibody or mixtures of antibodies can be used as well.

Of particular interest are therapeutic compositions which have at least two human monoclonal antibodies, usually at least three, more usually at least four, frequently at least seven and may have ten or more. Of particular interest are combinations of at least two human monoclonal antibodies which specifically react with at least two of the Fisher immunotypes, more particularly at least two of the Fisher immunotypes 1, 2, 3, 4, 5, 6 and 7, and preferably at least four. Preferred compositions react with at least four of the Fisher immunotypes, more preferred five to six and most preferred, all seven.

The mole ratio of the various components will usually not differ by more than a factor of 10, more usually by not more than a factor of 5, and will usually be in a mole ratio of about 1:1–2 to each of the other components.

The human monoclonal antibodies and pharmaceutical compositions thereof of this invention are particularly useful for oral or parenteral administration. Preferably, the pharmaceutical compositions may be administered parenterally, i.e., subcutaneous, intramuscular or intravenous. Thus, this invention provides compositions for parenteral administration which comprise a solution of the human monoclonal antibody or a cocktail thereof dissolved in an acceptable carrier, preferably an aqueous carrier. A variety of aqueous carriers can be used, e.g., water, buffered water, 0.4% saline, 0.3% glycine and the like. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, tonicity adjusting agents and the like, for example sodium acetate, sodium chloride, potassium chloride, calcium chloride, sodium lactate, etc. The concentration of antibody in these formulations can vary widely, i.e., from less than 0.5% usually 1% to as much as 15 or 20% by weight and will be selected primarily based on fluid volumes, viscosities, etc., preferably for the particular mode of administration selected.

Thus, a typical pharmaceutical composition for intramuscular injection could be made up to contain 1 ml sterile buffered water, and 50 mg of monoclonal antibody. A typical composition for intraveneous infusion could be made up to contain 250 ml of sterile Ringer's solution, and 150 mg of monoclonal antibody. Actual methods for preparing parenterally administrable compositions will be known or apparent to those skilled in the art and are described in more detail in, for example, *Remington's Pharmaceutical Science,* 15th Ed., Mack Publishing Company, Easton Pennsylvania (1975), which is incorporated herein by reference.

The monoclonal antibodies of this invention can be lyophilized for storage and reconstituted in a suitable carrier prior to use. This technique has been shown to be effective with conventional immune globulins and art-known lyophilization and reconstitution techniques can be employed. It will be appreciated by those skilled in the art that lyophilization and reconstitution can lead to varying degrees of antibody activity loss (e.g., with conventional immune globulins, IgM antibodies tend to have greater activity loss than IgG anitbodies) and that use levels may have to be adjusted to compensate.

The compositions containing the present human monoclonal antibody or a cocktail thereof can be administered for the prophylactic and/or therapeutic treatment of gram-negative bacterial disease. In therapeutic application, compositions are administered to a patient already infected with gram-negative bacteria, in an amount sufficient to cure or at least partially arrest the infection and its complications. An amount adequate to accomplish this is defined as a "therapeutically effective dose." Amounts effective for this use will depend upon the severity of the infection and the general state of the patient's own immune system but generally range from about 1 to about 200 mg of antibody per kilogram of body weight with dosages of from 5 to 25 mg per kilogram being more commonly used. It must be kept in mind that the materials of this invention may generally be employed in serious disease states, that if life-threatening or potentially life-threatening situations especially bacteremia and endotoxemia. In such cases, a view of the absence of extraneous substances, and the absence of "foreign substance" rejections, which are achieved by the present human monoclonal antibodies of this invention, it is possible and may be felt desirable by the treating physician to administer substantial excesses of these antibodies.

In prophylactic applications, compositions containing the present antibody or a cocktail thereof are administered to a patient not already infected by a gram-negative bacteria to enhance the patient's resistance to such potential infection. Such an amount is defined to be a "prophylactically effective dose." In this use, the precise amounts again depend upon the patient's state of health and general level of immunity, but generally range from 0.1 to 25 mg per kilogram, especially 0.5 to 2.5 mg per kilogram.

Single or multiple administrations of the compositions can be carried out with does levels and pattern being selected by the treating physician. In any event, the pharmaceutical formulations should provide a quantity of the antibody(ies) of this invention sufficient to effectively treat the patient.

Although the foregoing invention has been described in some detail by way of illustration and example for purposes of clarity of understanding, it will be obvious that certain changes and modifications may be practiced within the scope of the appended claims.

What is claimed is:

1. A protective human monoclonal antibody specifically binding with a serotypic determinant on the accessible lipopolysaccharide molecules of a Pseudomonas aeruginosa bacterium.
2. A human monoclonal antibody according to claim 1, wherein the bacterium is a member of one of the Fisher immunotypes 1 to 7.
3. A composition comprising at least two protective human monoclonal antibodies, each of said monoclonal antibodies binding with serotypic determinant on the lipopolysaccharide molecules of different Pseudomonas aeruginosa bacteria, wherein said monoclonal antibodies are present at concentrations greater than naturally occurring in human sera.
4. A composition according to claim 3, wherein the human monoclonal antibodies bind with serotype determinants of one of the bacterial IATS types 1 to 17.
5. A composition according to claim 4, wherein said monoclonal antibodies bind with the same serotypes of the same bacterial species.
6. A composition according to claim 3, wherein said antibodies bind with the lipopolysaccharides of at least two of the Fisher immunotypes 1 to 7.
7. A pharmaceutical composition comprising a composition according to any of claims 1, 2, 3, 4, 5 or 6 and a physiologically acceptable carrier.
8. An immortal transformed human lymphocyte cell line which secretes a protective human monoclonal antibody specifically binding with a serotypic determinant on the accessible lipopolysaccharide molecules of a Pseudomonas aeruginosa bacterium.
9. A cell line according to claim 8 wherein the bacterium is an IATS serotype 1 to 17.
10. A cell line according to claim 8, wherein said bacterium is a Fisher immunotype 1 to 7.
11. A cell line according to claim 10, which is one of A.T.C.C. No. CRL 8562, CRL 8752, CRL 8753, CRL 8754, CRL 8795, CRL 8796, or CRL 8797.
12. A method (for treating a mammalian host susceptible to bacteremia) which comprises:
    administering a prophylactic or therapeutic amount to said host of a composition according to any of claims 1, 2, 3, 4, or 5.
13. A method (for treating a mammalian host susceptible to bacteremia which comprises:
    administering a prophylactic or therapeutic amount to said host of a composition according to any of claim 6.
14. A human monoclonal antibody according to claim 1, wherein the bacterium is a member of the IATS serotypes 1 to 17.
15. A composition according to claim 3, wherein said monoclonal antibodies are lyophilized.

* * * * *